United States Patent
Chang

(10) Patent No.: US 8,258,946 B2
(45) Date of Patent: Sep. 4, 2012

(54) MULTIFUNCTIONAL ELECTRONIC DEVICE AND METHOD FOR USING THE SAME

(75) Inventor: Che-Jui Chang, Taipei Hsien (TW)

(73) Assignee: FIH (Hong Kong) Limited, Kowloon (HK)

( * ) Notice: Subject to any disclaimer, the term of this patent is extended or adjusted under 35 U.S.C. 154(b) by 418 days.

(21) Appl. No.: 12/563,240

(22) Filed: Sep. 21, 2009

(65) Prior Publication Data

US 2010/0123577 A1    May 20, 2010

(30) Foreign Application Priority Data

Nov. 20, 2008  (CN) .......................... 2008 1 0305659

(51) Int. Cl.
 *G08B 21/00*  (2006.01)
(52) U.S. Cl. .................... 340/540; 340/568.1; 340/539.1
(58) Field of Classification Search .................. 340/540, 340/539.11, 539.22, 539.24, 539.26, 539.12, 340/566, 636.14, 636.18, 568.1, 572.1, 572.8, 340/531, 539.1
See application file for complete search history.

(56) References Cited

U.S. PATENT DOCUMENTS

| 6,190,314 | B1 | 2/2001 | Ark et al. | |
| 7,109,859 | B2 * | 9/2006 | Peeters | .................... 340/539.11 |
| 2001/0044588 | A1 * | 11/2001 | Mault | ........................... 600/549 |
| 2002/0083122 | A1 | 6/2002 | Lemchen | |
| 2003/0149344 | A1 | 8/2003 | Nizan | |
| 2006/0063980 | A1 * | 3/2006 | Hwang et al. | .................. 600/300 |
| 2007/0270665 | A1 * | 11/2007 | Yang et al. | ..................... 600/300 |

FOREIGN PATENT DOCUMENTS

| CN | 1739445 A | 3/2006 |
| CN | 101112305 A | 1/2008 |
| WO | WO99/51144 A1 | 10/1999 |

* cited by examiner

*Primary Examiner* — Daniel Previl

(74) *Attorney, Agent, or Firm* — Altis Law Group, Inc.

(57) ABSTRACT

An electronic device includes a detecting module, a processor module, a reminding module and a parameter module. The detecting module includes at least one detecting sensor installed on the electronic device, such that a user contacts the detecting sensor when operating the electronic device. The parameter module stores predetermined acceptable ranges of physiological parameters of users. The detecting module detects physiological parameters of the user operating the electronic device via the detecting sensor, the processor module compares the detected physiological parameters with the acceptable ranges and controls the reminding module to remind the user to relax when at least one physiological parameter is outside of the acceptable range.

17 Claims, 2 Drawing Sheets

MULTIFUNCTIONAL ELECTRONIC DEVICE AND METHOD FOR USING THE SAME

BACKGROUND

1. Technical Field

The present disclosure relates to electronic devices, and particularly to a multifunctional electronic device and a method for using the same.

2. Description of Related Art

Nowadays, electronic devices, such as mobile phones, personal digital assistants (PDA) and laptop computers, are widely used. Many users usually spend a great amount of time operating electronic devices during work or pleasure. Thus, the users may become tired, and harmed by electromagnetic radiation generated by the electronic devices.

Some conventional electronic devices are provided with the function of reminding users to rest for protecting the users from tiredness and electromagnetic radiation. For example, an electronic device outputs an alerting signal (e.g. sounds, vibrations, etc) in a predetermined time to remind the user thereof to take a break. However, most conventional electronic devices cannot detect the health statuses of users and remind the users according to their personal health statuses. For example, if a user operating a conventional electronic device is ill and needs to rest immediately, the electronic device does not remind the user to rest until the predetermined reminding time.

Therefore, there is room for improvement within the art.

BRIEF DESCRIPTION OF THE DRAWINGS

Many aspects of the present multifunctional electronic device and method for using the same can be better understood with reference to the following drawings. The components in the various drawings are not necessarily drawn to scale, the emphasis instead being placed upon clearly illustrating the principles of the present multifunctional electronic device and method for using the same. Moreover, in the drawings, like reference numerals designate corresponding parts throughout the figures.

DETAILED DESCRIPTION

Figure 1:
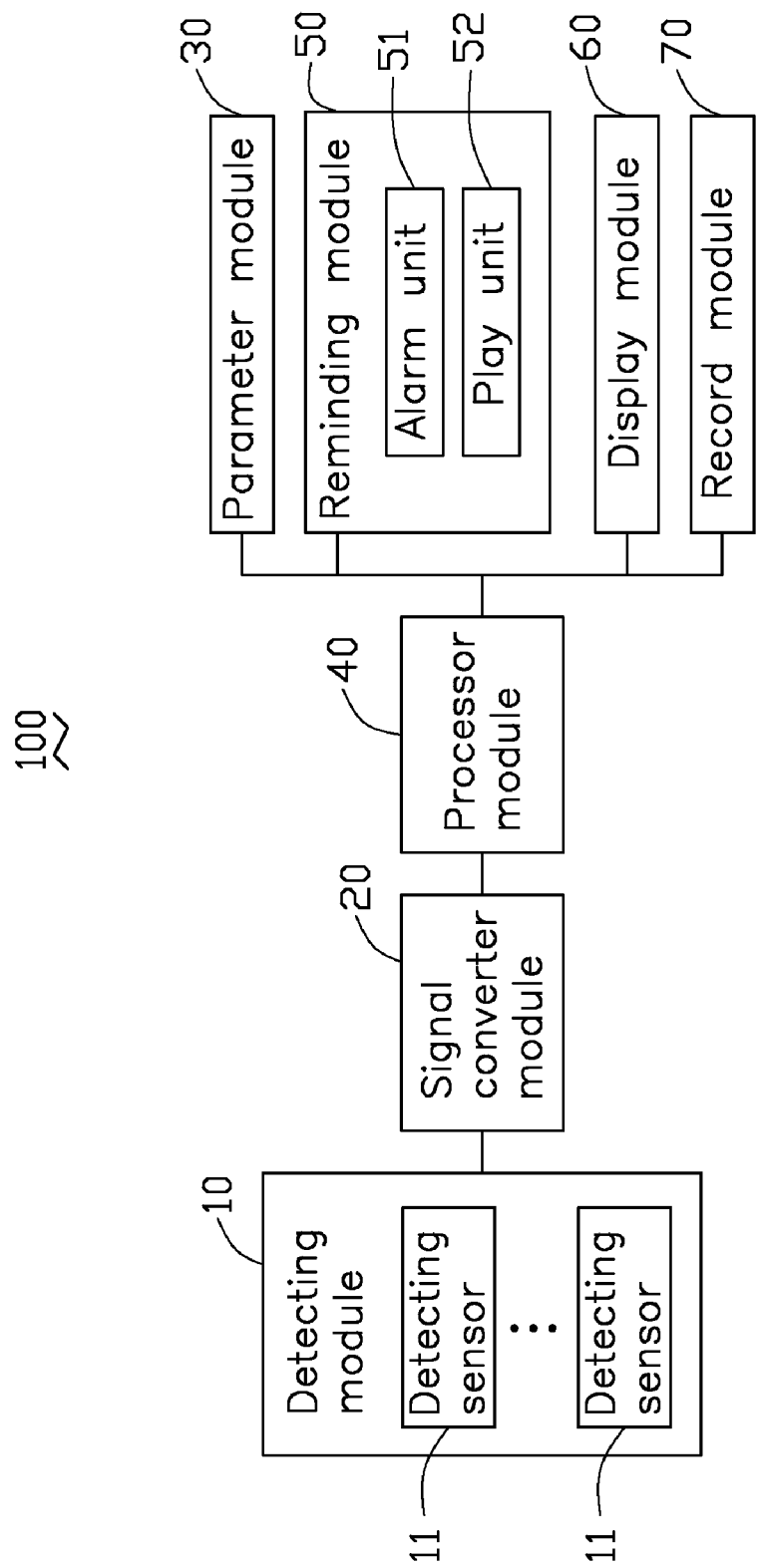
FIG. 1 is a block diagram of a multifunctional electronic device, according to an exemplary embodiment.

FIG. 1 shows a multifunctional electronic device 100 according to an exemplary embodiment. The multifunctional electronic device 100 can be a mobile phone, a personal digital assistant (PDA), a laptop computer, etc. The electronic device 100 includes a detecting module 10, a signal converter module 20, a parameter module 30, a processor module 40, a reminding module 50, a display module 60 and a record module 70. The detecting module 10, the signal converter module 20 and the processor module 40 are electronically connected together in series. The parameter module 30, the reminding module 50, the display module 60 and the record module 70 are all electronically connected to the processor module 40.

The detecting module 10 is used to detect physiological parameters of users operating the electronic device 100. Particularly, the detecting module 10 can be a cardiotachometer, a thermometer, an ohmmeter, or a combination of these apparatuses. The detecting module 10 includes at least one detecting sensor 11 installed on outside portions of the electronic device 100 directly contacted by the users (e.g., keypad, button, touch panel, mouse, etc.). In use, the detecting sensors 11 directly contact the bodies of the users, thus the detecting module 10 can detect physiological parameters of the users (e.g., cardiotaches, temperatures, body resistances, etc.) and generate electronic signals corresponding to these parameters without any action by the user.

The signal converter module 20 can be a typical analog/digital (A/D) converter and is used to convert the electronic signals generated by the detecting module 10 into digital signals.

The parameter module 30 is a storage used to store predetermined acceptable ranges of physiological parameters of users detected by the detecting module 10. For example, a common acceptable range of cardiotach is about 60-100 beats per minute.

The processor module 40 can be a central processing unit (CPU) of the electronic device 100. The processor module 40 receives digital signals corresponding to the physiological parameters of the users from the signal converter module 20, and then compares the physiological parameters of the users within the stored predetermined acceptable ranges. Thus, the health statuses of the users can be automatically detected.

The reminding module 50 includes an alarm unit 51 and a play unit 52, which are both connected to the processor module 40. The alarm unit 51 can be a speaker, a light emitting diode (LED), a vibrating device, etc., or a combination of these apparatuses. When the detected physiological parameters of the users exceed the acceptable ranges, the processor module 40 controls the alarm unit 51 to alert the users (e.g., by means of sound, flashing or vibration). The play unit 52 can be a multimedia processor and is used to play music or actuate a game to relax the users.

The display module 60 can be a typical display, which is used to display detected physiological parameters of the users and the results of comparing the detected physiological parameters with the acceptable ranges. The record module 70 is a storage used to store the detected physiological parameters of the users and the comparing results. Understandably, both the parameter module 30 and the record module 70 can be typical storages of the electronic device 100.

Figure 2:
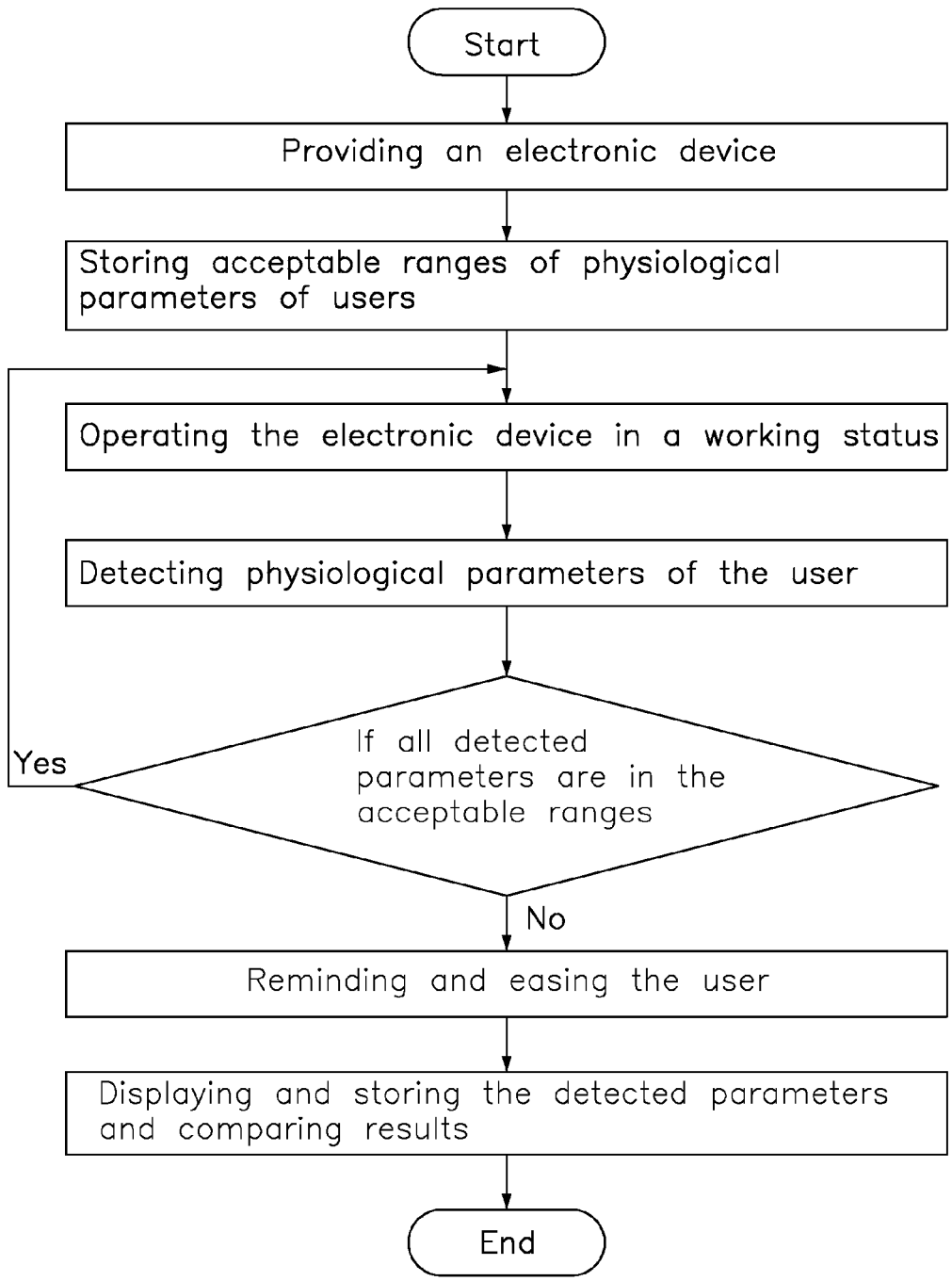
FIG. 2 is a flow chart of a working method of the multifunctional electronic device shown in FIG. 1.

Also referring to FIG. 2, a method for using the electronic device 100 is provided. The method includes the steps as follows.

First, an electronic device 100 is provided, and predetermined acceptable ranges of physiological parameters (e.g., cardiotaches, temperatures, body resistances, etc.) of users are set and stored in the parameter module 30. The data can be input into the parameter module 30 via typical input apparatuses (e.g., keypad, button, touch panel, etc.) of the electronic device 100. Additionally, the processor unit 40 can also receive inputted acceptable ranges of physiological parameters of users and transmit the ranges to the parameter module 30 to store.

When at least one user operates the electronic device 100 via typical input portions of the electronic device 100 (e.g., keypad, button, touch panel, mouse, etc.), the electronic device 100 enters a conventional working status. At the same time, the detecting sensors 11 installed on the input portions detects the physiological parameters (e.g., cardiotaches, temperatures, body resistances, etc.) of the user by contacting with the users, and then the detecting module 10 generates electronic signals corresponding to these parameters.

The electronic signals are then transmitted to the signal converter module 20. The signal converter module 20 converts the electronic signals into digital signals and transmits the digital signals to the processor module 40. Thus, the processor module 40 obtains the current physiological parameters of the user.

The processor module 40 then compares the detected physiological parameters of the user with the acceptable ranges stored in the parameter module 30. If all detected physiological parameters are in the acceptable ranges, the electronic device 100 remains in the same working status. If at least one detected physiological parameter of the user is outside of the acceptable range, the processor module 40 determines that the user may be ill and should rest immediately. Thus, the processor module 40 controls the alarm module 51 to output an alerting signal, such that the user can be immediately alerted. Furthermore, the processor module 40 can control the play unit 52 to play music or actuate a game to relax the user. Finally, the detected physiological parameters and the comprising results are displayed by the display module 60 and stored in the record module 70 for inquiry.

Understandably, when the user keeps operating the electronic device 100, the detecting module 10 can continuously detect the physiological parameters of the user in a predetermined frequency. Correspondingly, the processor module 40 can continuously determine if the user may be ill in the predetermined frequency. If the user may be ill, the processor module 40 can control the alarm module 51 to continuously alerting until the user rests.

The electronic device 100 can instantaneously detect physiological parameters of its users and determine the health statuses of the users according to the detecting results. When a user operating the electronic device 100 may be ill, the electronic device 100 can immediately alert the user to take a break, and can also record current physiological parameters of the user for inquiry.

It is to be further understood that even though numerous characteristics and advantages of the present embodiments have been set forth in the foregoing description, together with details of structures and functions of various embodiments, the disclosure is illustrative only, and changes may be made in detail, especially in matters of shape, size, and arrangement of parts within the principles of the present invention to the full extent indicated by the broad general meaning of the terms in which the appended claims are expressed.

What is claimed is:

1. An electronic device, comprising:
    a detecting module including at least one detecting sensor installed on input portions of the electronic device and configured to be contacted by a user when the user operates the electronic device using the input portions;
    a processor module electronically connected to the detecting module;
    a reminding module electronically connected to the processor module wherein the reminding module includes a play unit electronically connected to the processor module, and the processor module controls the play unit to relax the user when at least one physiological parameter is outside of the acceptable range; and
    a parameter module electronically connected to the processor module and storing predetermined acceptable ranges of physiological parameters of users; wherein the detecting module detects physiological parameters of the user operating the electronic device via the detecting sensor, the processor module compares the detected physiological parameters with the acceptable ranges and controls the reminding module to remind the user when at least one physiological parameter is outside of the acceptable range.

2. The electronic device as claimed in claim 1, wherein the detecting module is any one of a cardiotach ometer, a thermometer, an ohmmeter, or a combination of these apparatuses.

3. The electronic device as claimed in claim 1, wherein the reminding module includes an alarm unit electronically connected to the processor module, and the processor module controls the alarm unit to alarm the user when at least one physiological parameter is outside of the acceptable range.

4. The electronic device as claimed in claim 3, wherein the alarm unit is any one of a speaker, a light emitting diode (LED), a vibrator, or a combination of these apparatuses.

5. The electronic device as claimed in claim 1, wherein the play unit is a multimedia processor, and the processor module controls the play unit to play music or actuate a game to relax the user when at least one physiological parameter is outside of the acceptable range.

6. The electronic device as claimed in claim 1, further comprising a signal converter module electronically connected between the detecting module and the processor module.

7. The electronic device as claimed in claim 1, further comprising a display module electronically connected to the processor module to display the detected physiological parameters of the user and the compared results.

8. The electronic device as claimed in claim 1, further comprising a record module electronically connected to the processor module to store the detected physiological parameters of the user and the compared results.

9. The electronic device as claimed in claim 1, wherein the detecting sensor is installed on any one selected from a keypad, a button, a touch panel, and a mouse of the electronic device.

10. A method for using an electronic device, comprising these steps:
    storing predetermined acceptable ranges of physiological parameters of users in the electronic device;
    a user operating the electronic device using input portions of the electronic device, and contacting at least one detecting sensor installed on the input portions;
    detecting physiological parameters of the user operating the electronic device as the user operates the electronic device and contacts the detecting sensor;
    comparing the detected physiological parameters of the user with the acceptable ranges; and
    reminding the user when at least one detected physiological parameter of the user is outside of the acceptable range wherein the reminding module includes a play unit electronically connected to the processor module, and the processor module controls the play unit to relax the user when at least one physiological parameter is outside of the acceptable range.

11. The method as claimed in claim 10, wherein the physiological parameters includes cardiotaches, temperatures and body resistances of users.

12. The method as claimed in claim 10, further comprising a step of switching the electronic device to a working status when operating the device.

13. The method as claimed in claim 12, further comprising a step of keeping the electronic device in the working status when all detected physiological parameters are within their acceptable ranges.

14. The method as claimed in claim 10, further comprising a step of relaxing the user when at least one detected physiological parameter of the user is outside of the acceptable range.

15. The method as claimed in claim 10, further comprising a step of displaying the detected physiological parameter of the user and the compared results.

16. The method as claimed in claim 10, further comprising a step of storing the detected physiological parameter of the user and the compared results.

17. The method as claimed in claim 10, further comprising installing the detecting sensor on any one selected from a keypad, a button, a touch panel, and a mouse of the electronic device.

* * * * *